United States Patent [19]

Wass et al.

[11] Patent Number: 5,349,945
[45] Date of Patent: Sep. 27, 1994

[54] AEROSOL DISPENSER COMPRISING AN INDICATOR ASSEMBLY

[75] Inventors: Anthony C. L. Wass, Lincs; Brian R. Law, Leicester, both of United Kingdom

[73] Assignee: Minnesota Mining and Manufacturing Company, St. Paul, Minn.

[21] Appl. No.: 790,373

[22] Filed: Nov. 12, 1991

[30] Foreign Application Priority Data

Nov. 26, 1990 [GB] United Kingdom ............... 9025654

[51] Int. Cl.$^5$ .......................................... A61M 11/00
[52] U.S. Cl. .......................... 128/200.23; 128/200.14; 128/203.15
[58] Field of Search .................. 128/200.14, 200.18, 128/200.23, 203.12, 203.15; 222/48, 23, 402.1, 402.13

[56] References Cited

U.S. PATENT DOCUMENTS 5,020,527  6/1991  Dessertine .............. 128/200.23

FOREIGN PATENT DOCUMENTS 0269496   6/1988  European Pat. Off. .
1058636   2/1967  United Kingdom .
1290484   9/1972  United Kingdom .
2063075   6/1981  United Kingdom .
2191032A 12/1987  United Kingdom .
WO91/06334 5/1991 World Int. Prop. O. .

Primary Examiner—Vincent Millin
Assistant Examiner—Raleigh W. Chiu
Attorney, Agent, or Firm—Gary L. Griswold; Walter N. Kirn; Dale E. Hulse

[57] ABSTRACT

An aerosol dispenser for use with an aerosol vial. The dispenser contains an assembly that indicates the quantity of doses dispensed from or remaining in the aerosol vial. The assembly comprises a rotatable indicator comprising a circumferential rack that is engaged by a worm-gear. Reciprocal movement of an aerosol vial within the dispenser causes rotation of the worm-gear which in turn causes rotation of the rack.

16 Claims, 4 Drawing Sheets

AEROSOL DISPENSER COMPRISING AN INDICATOR ASSEMBLY

This invention relates to devices for indicating the quantity of doses dispensed from and/or remaining in an inhalation device and in particular to inhalation devices by which medicaments contained in a pressurised aerosol vial are administered to a patient.

Certain devices that are operated by a reciprocating element, e.g., a button, require the presence of a counting device in order to provide an indication of the extent of use. Known counting devices range from complex electrical devices providing a visual digital display to simple mechanical devices having a sliding scale to display the extent of use.

Inhalation therapy is becoming an increasingly important method of administering medicaments to a patient. The medicament is formulated with suitable propellant and appropriate other components and charged in an aerosol vial. The aerosol vial is fitted with a valve which generally comprises a metering chamber such that each operation of the valve dispenses a predetermined measured quantity of medicament. The aerosol vial is inserted into an adaptor having a mouthpiece or a port adapted for nasal use and the medicament is administered by firing the aerosol simultaneously with inhalation. Examples of such inhalation devices are the MEDIHALER ™ and AUTOHALER ™ aerosol inhalation devices commercially available from Minnesota Mining and Manufacturing Company.

With a conventional press-and-breathe device in which the patient fires the device by depressing the aerosol vial whilst inhaling, a rough indication of the amount of medicament remaining in the vial can be obtained by shaking the whole unit. With experience, the user can distinguish the difference in 'feel' between a vial that is substantially full and one that is substantially empty. However, this method is necessarily far from precise and is even less satisfactory with a breath actuated inhaler in which, because of the additional parts, the mass of the aerosol contents is a smaller proportion of the total unit weight.

With inhalation devices that utilize an aerosol vial initially charged with a known quantity of medicament, a metered dose of which is dispensed each time the vial is operated, counting the number of operations of the valve will give an indication of the total amount of medicament dispensed and hence the amount of medicament remaining in the vial. The metering is normally accurate but incorrect actuation of the vial occasionally results in a reduced dose. The dose, however, can never exceed the predetermined metered quantity. Therefore counting the number of doses used is a safe basis for computing the number of doses remaining because any error will indicate the presence of fewer doses than are actually present. It is highly desirable that the patient be given an indication that the contents of the vial are being depleted before the vial is actually empty and the patient attempts to use the empty inhaler at a time when the patient is under stress. Accordingly, it is desirable to incorporate some form of counting device on the aerosol vial or adaptor which will give an indication before the vial is empty.

A conventional aerosol vial is operated by causing a valve stem to be depressed relative to the vial body. A convenient means of counting the number of discharges from the aerosol vial is to convert the reciprocatory movement of the valve stem into one-way movement of some form of indicator. If the number of doses contained within the vial were relatively small, it would be possible to use the linear movement of the vial to index along a simple indicator band and so mark the progression from "full" to "empty". Such a counting means need only comprise a ratchet device and a toothed indicator rack moving in a direction parallel to the reciprocal motion of the valve stem. However, the number of doses normally number at least fifty, often two hundred. Accordingly, in practice the total linear movement of such a rack would be far too great to be accommodated in a conventional inhaler unless each incremental step of the rack were very small. However, tiny incremental steps require firstly that only a small fraction of the total reciprocatory movement of the valve stem is converted into rack movement and secondly very fine teeth must be moulded on both mating parts. These requirements are not easy to fulfill economically and on a mass production basis. Even if such fine teeth were readily mouldable with such precision, the slightest distortion would lead to the indicator rack either not being indexed at all or indexed by two or more increments for a given single actuation. Such an inaccurate counting device would serve no useful purpose.

In an alternative arrangement, the rack can take the form of an indicator wheel or a counter ring mounted for rotational movement in response to the reciprocal movement of the valve stem. The rack can be rotatable about an axis either transverse or parallel to the direction of valve movement.

British Published Patent Application No. 2191032A discloses an indicator assembly for use with aerosol dispensers of the press-and-breathe type comprising a housing mounted on the exterior of the dispenser and defining a compartment containing a ratchet wheel and a ratchet wheel driving member movable with the aerosol vial to cause rotation of the ratchet wheel; and a rotatable toothed indicator wheel mounted for rotation about an axis transverse or substantially transverse to the movement of the aerosol vial. The ratchet wheel is provided with a spur gear which meshes with the indicator wheel to cause rotation of the same. The indicator wheel is provided with suitable markings to provide the user with a visual impression of the quantity of doses dispensed from the vial. One revolution of the indicator wheel would permit much greater total movement within the confines of a normal inhaler configuration than any purely linear movement. Aerosol vials, however, may contain up to 200 doses. It would be difficult to provide so many teeth on a small circular rack. It would therefore be necessary to reduce the number of teeth and allow the rack to rotate through a number of revolutions before the aerosol vial was empty. However, this arrangement would require some means of counting the revolutions of the rack.

British Patent Specification No. 1290484 discloses an aerosol dispenser of the press-and-breath type having an indicator assembly comprising two coaxial, toothed indicator rings spaced in parallel planes and mounted for rotation within the dispenser housing about an axis substantially parallel to the direction of valve movement, one of which rings is rotatable by the other at a fraction of the rotational displacement thereof; and a sleeve slidably mounted within the dispenser housing which receives and is movable with the aerosol vial. Displacement of the aerosol vial at device actuation causes the sleeve to engage and rotate one of the two rings so as to indicate to the user that a dose has been dispensed from the vial. At least one of the counter rings is provided with markings viewed through a window in the dispenser housing to provide a visual indication to the user of the quantity of doses dispensed from the aerosol vial. However, such a device still relies on the relatively coarse movement of the aerosol vial to effect rotation of the indicator ring(s). Furthermore, as the function of the indicator assembly is simply to give an indication to the user when the vial is approaching the empty condition, a large amount of rack movement is unnecessary. It would be highly desirable to arrange that the indicator ring did not move through more than one revolution so that one end of the arc of movement could carry the indication "FULL" and the other end of the arc of movement could carry an "EMPTY" indication. Heretofore there is no known simple counting device meeting these requirements.

According to the present invention there is provided an aerosol dispenser comprising a housing having a patient port, the housing being adapted to accommodate an aerosol vial equipped with a metered-dose dispensing valve that comprises a valve stem movable between closed and discharge positions, the dispenser further comprising a support block having a socket adapted to receive the stem of the valve and an orifice having open communication with the socket and the patient port, the aerosol vial and support block being reciprocally movable relative to each other to cause the stem to move to its discharge position, thereby dispensing a dose from the aerosol vial, the dispenser having an indicator assembly comprising rotatable indicator means to provide an indication of the quantity of doses dispensed from or remaining in the aerosol vial, the indicator means comprising a circumferential rack and being mounted for rotation about an axis parallel or substantially parallel to said reciprocal movement of the vial and support block; a worm-gear engaging said circumferential rack and a movement detecting member movable in response to said reciprocal movement of the vial and support block, wherein movement of the movement detecting member in response to said reciprocal movement causes rotation of said worm gear and indicator means.

Indicator assemblies for use in the present invention comprise counting devices for aerosol dispensers, wherein the linear (and often rather coarse) movement of an aerosol vial relative to its support block, or vice versa, used to dispense a single dose from the vial is translated via a worm (reduction) gear into a much smaller incremental movement of a rotable indicator means to provide a visual indication of the total quantity of doses dispensed from, or remaining in, that aerosol vial. The conversion of linear to rotary movement together with permanent engagement of the worm gear and indicator means is found to provide a reliable counting device.

While such counting devices can be fitted to a wide range of aerosol dispensers, they are most suitable for use with metered-dose inhalers, i.e., dispensers that are used in connection with a aerosol vial containing a self-propelled pharmaceutical formulation comprising a medicament, the vial being equipped with a valve that dispenses a metered dose of a medicament for inhalation by a patient. The counting device can be used with both press-and-breathe metered dose inhalers and breath actuated metered dose inhalers.

The indicator means generally comprises a circular or annular rack. The rack is generally mounted for rotation about whichever of the aerosol vial and support block is held stationary and is provided with a plurality of circumferential, generally equally-spaced teeth that mesh with the worm of the reduction gear. The teeth can project radially inward or radially outward. The indicator rack is preferably provided with suitable markings to indicate to the patient the quantity of doses dispensed from or remaining in the aerosol vial. The teeth of the indicator rack preferably include a spacer gap and/or a spacer block to halt its rotation at a given point or to prevent more than one full revolution of the rack.

The housing of the dispenser can be provided with a viewing port through which the indicator means is visible. Alternatively the indicator means can be viewed through the patient port. In one embodiment the viewing port comprises a window of a transparent, optionally magnifying, material.

The worm gear generally comprises a shaft bearing a worm and having an integral ratchet wheel that is selectively engaged by the movement detecting member to cause rotation of the worm gear. The shaft is normally mounted for rotation about an axis transverse or substantially transverse to the direction of reciprocal movement between the vial and support block. In a further embodiment, the worm and ratchet wheel can be integrated into a single 'toothed' worm. The pitch of the worm is selected such that rotary movement of the worm-gear produces a much smaller incremental movement of the indicator means. In this manner, a single revolution of the indicator means can cope with an aerosol vial containing several hundred doses of medicament.

The movement detecting member generally comprises a projecting finger that is selectively engageable with the ratchet wheel to cause rotation of the ratchet wheel and hence rotation of the worm gear. In one embodiment the finger is fixed relative to whichever of the aerosol vial and support block is movable relative to the other so that movement causes the finger to engage the ratchet wheel. In an alternative embodiment the projecting finger can be fixed relative to the stationary element (e.g., the support block) such that the displaced aerosol vial engages and displaces the projecting finger, thereby causing it to engage the worm gear. Alternatively, the movement detecting member can comprise the aerosol vial or the support block itself. For example, the cap or ferrule of the aerosol vial can, on relative movement of the vial, engage and rotate the ratchet wheel, thereby rotating the worm gear.

The indicator assembly can additionally comprise means to prevent unwanted movement of the indicator means. For example, the assembly can be provided with one or more fixed, 'non-return' fingers to prevent 'wrong-way' rotation of the worm gear and/or the indicator means during handling and transport and during return movement of the movement detecting member.

Preferably, the indicator assembly is constructed such that the patient (or any other person) cannot readily obtain access to the counting device. This prevents unauthorized or accidental tampering. In addition, the assembly is preferably constructed such that the aerosol vial can be readily removed from the dispenser housing for cleaning, freeing stem obstructions etc., without changing the position of the indicator means.

The invention will now be described with reference to the accompanying drawings in which.

Figure 6:
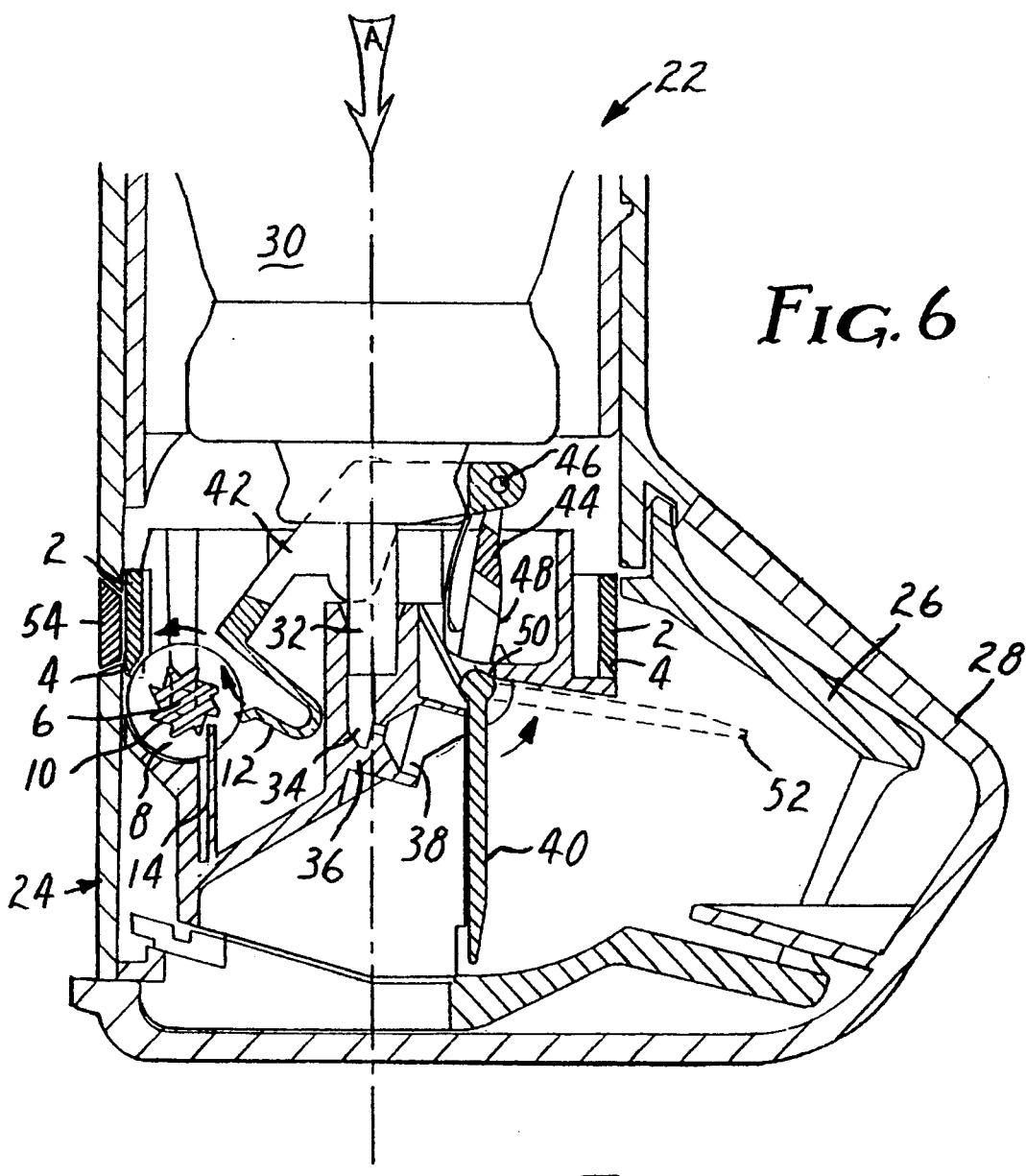
FIG. 6 is a vertical section through a breath-actuated, metered dose aerosol dispenser in accordance with the invention.
Figure 7:
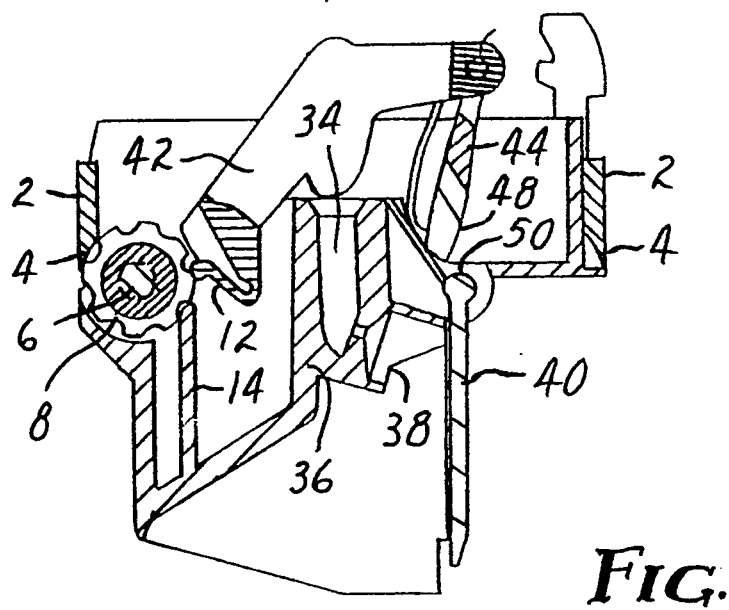
Figure 8:
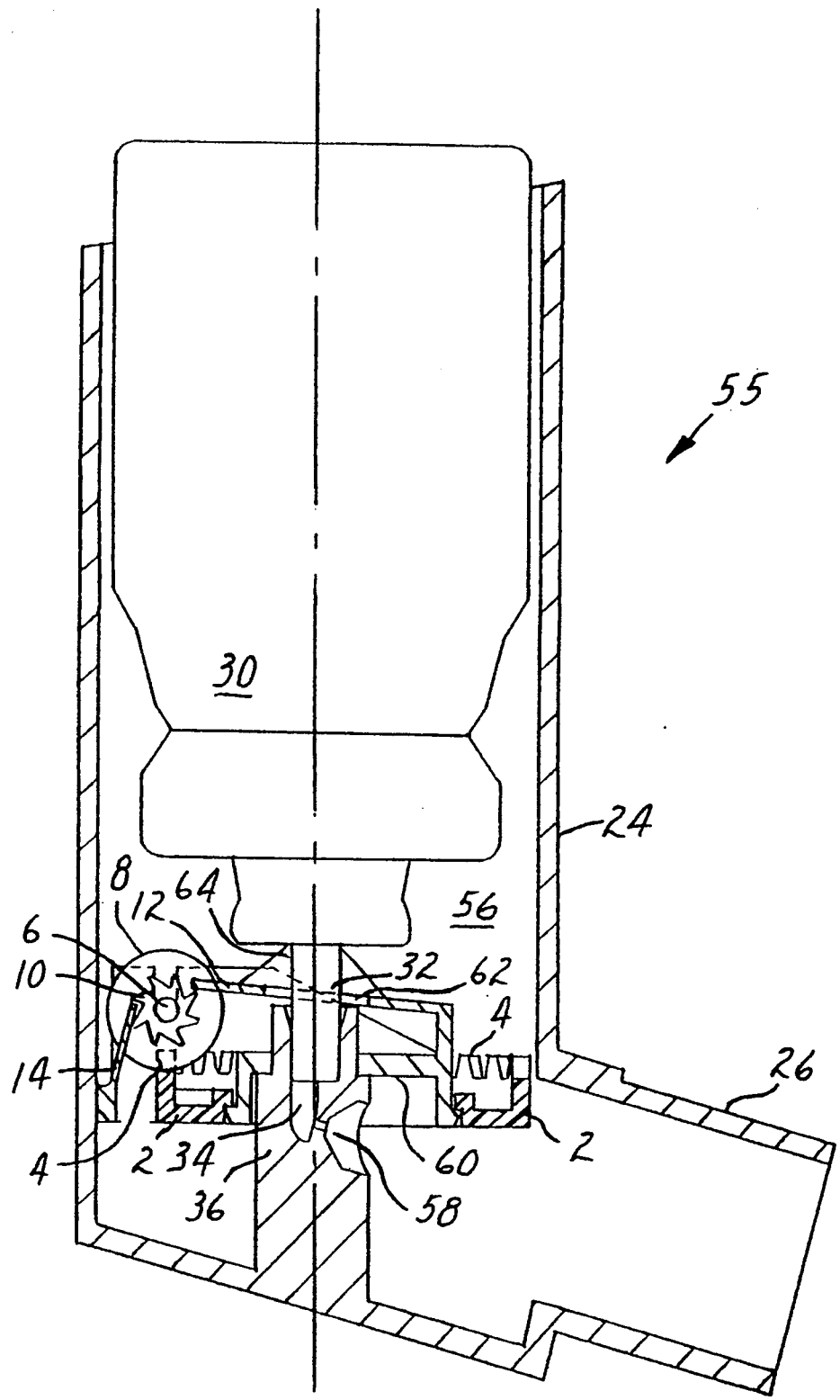
Figure 9:
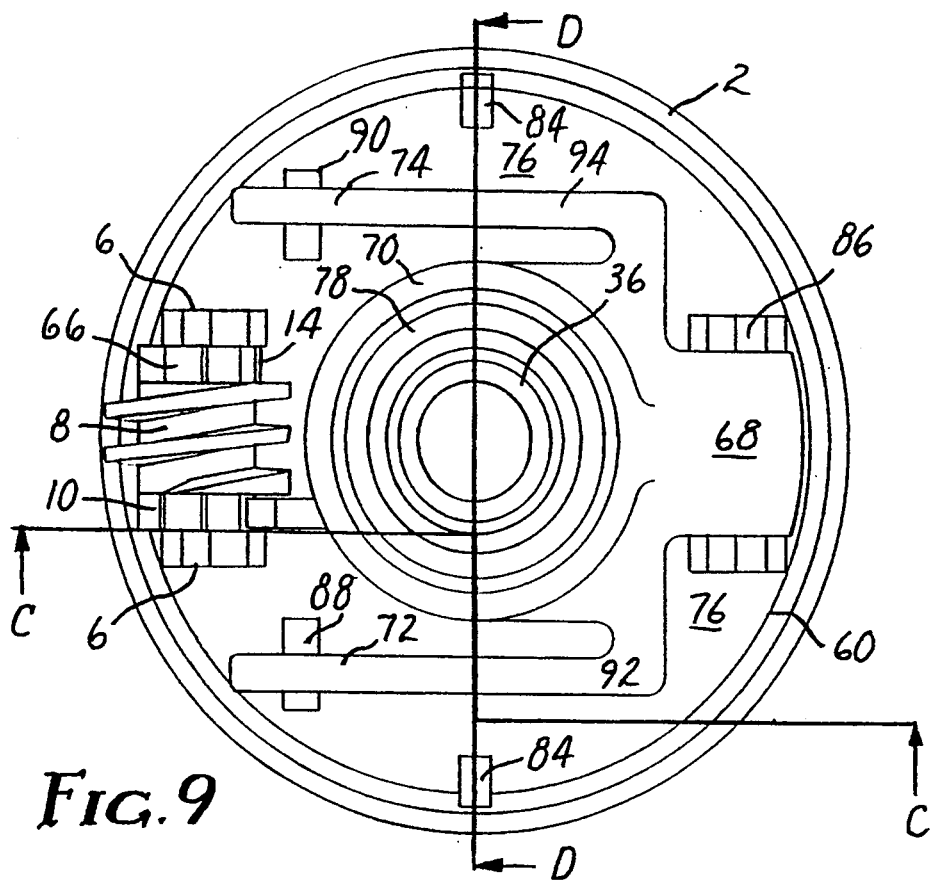
Figure 10:
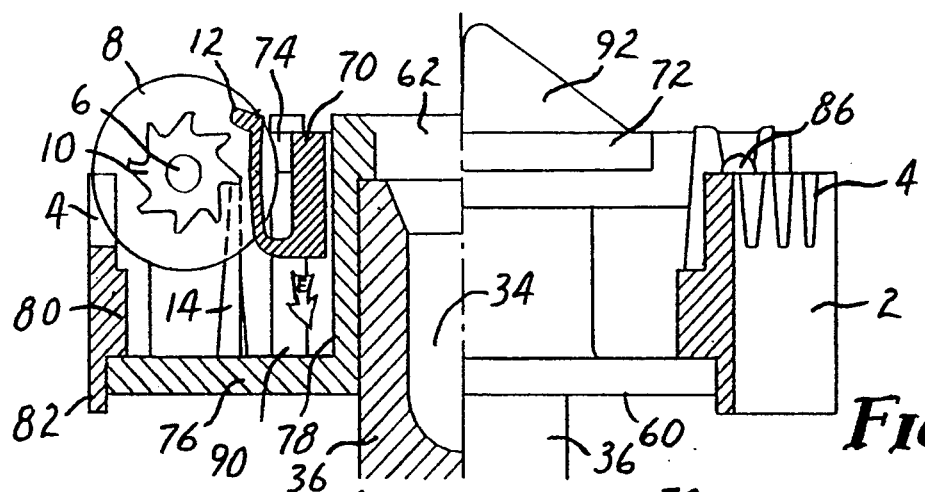
Figure 11:
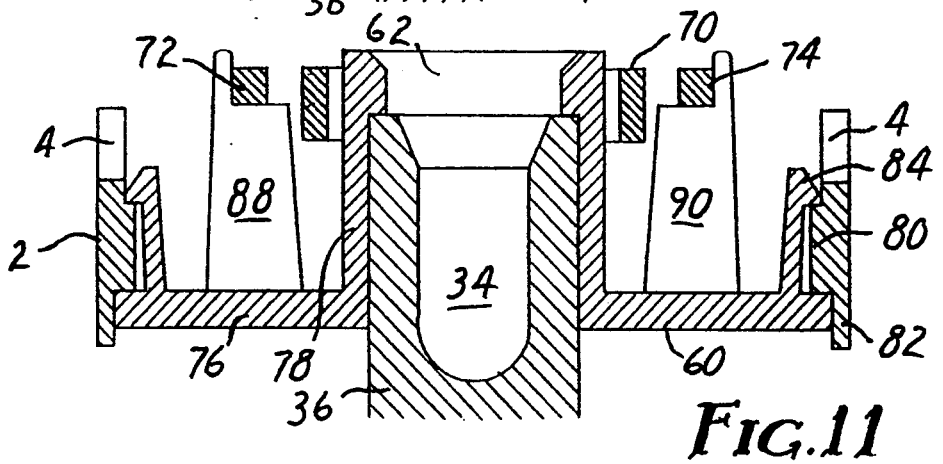

FIG. 7 is a sectional view through the support block of the aerosol dispenser shown in FIG. 6 fitted with an alternative indicator assembly, FIG. 8 is a vertical section through a press-and-breathe, metered dose inhaler in accordance with the invention, FIG. 9 is a horizontal section through the support block of an aerosol dispenser in accordance with the invention, FIG. 10 is a vertical section along the axis C—C of the support block of FIG. 9, and FIG. 11 is a vertical section along the axis D—D of the support block of FIG. 9.

FIGS. 1 to 5 represent a series of closely related indicator assemblies with each assembly shown isolated from its aerosol dispenser in order to more clearly illustrate the principles underlying the invention. Each assembly comprises indicator means in the form of a circumferential rack, hereinafter referred to as counter ring 2 having a plurality of circumferential teeth 4. Counter ring 2 is adapted to be rotated about an axis parallel or substantially parallel to the linear (reciprocal) movement of the aerosol vial and support block (denoted by center line A); and a worm (reduction) gear permanently engaging teeth 4 of counter ring 2 and adapted to be rotated about an axis transverse or substantially transverse to the movement of the vial and support block (denoted by centre line B).

Figure 1:
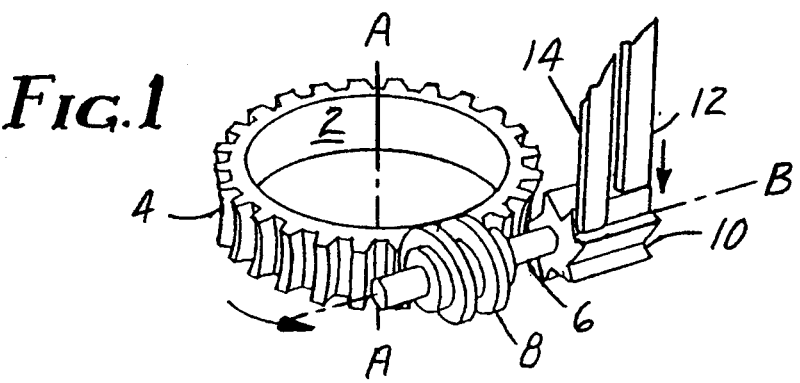
FIG. 1 is a perspective view of an indicator assembly suitable for use with an aerosol dispenser in accordance with the invention.

Referring to FIG. 1, the reduction gear comprises shaft 6 bearing worm 8 and integral ratchet wheel 10. Ratchet wheel 10 is selectively engaged by the movement detecting member in the form of 'actuating' finger 12, typically located on the aerosol vial or the support block, thereby rotating the reduction gear a predetermined distance. Worm 8 engages teeth 4 of counter ring 2 and converts the rotation of the reduction gear into incremental movement of the counter ring. The indicator assembly is preferably provided with 'non-return' finger 14 which ensures that the reduction gear is able to rotate in one direction only (in this case clockwise). Thus, linear movement of the aerosol vial can be converted into unidirectional incremental movement of the reduction gear which, in turn, is converted into unidirectional, incremental movement of the counter ring.

In order to reduce the size of the indicator assembly even further, thereby enabling it to be fitted into a wide range of commercially available press-and-breathe and breath actuated inhalers with the minimum of modifications, modifications as illustrated in FIGS. 2-5 have been made to the assembly shown in FIG. 1.

Figure 2:
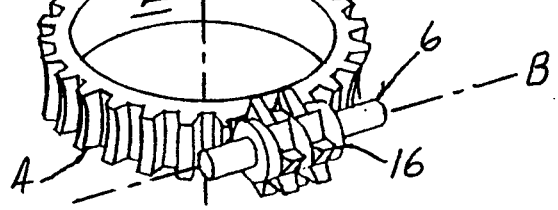
FIGS. 2 to 5 are perspective views of alternative arrangements of indicator assembly for use with aerosol dispensers in accordance with the invention.
Figure 3:
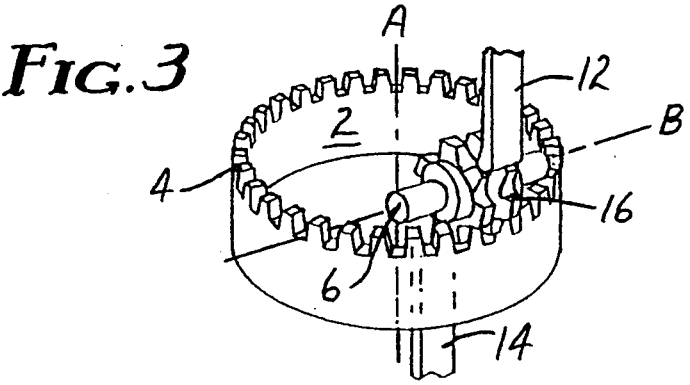
Figure 4:
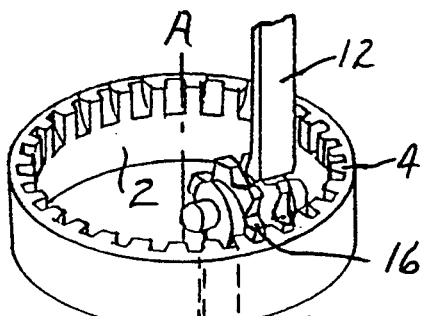

Referring to FIG. 2, the ratchet wheel and the worm of the reduction gear have been combined as 'toothed' worm 16 enabling both to be located on the center line of the indicator assembly (the actuating and non-return fingers have been omitted from the figure for reasons of clarity). The use of a combined worm/ratchet wheel allows teeth 4 of counter ring 2 to be oriented axially about its circumference (see FIG. 3) or radially inwards (see FIG. 4). This last arrangement allows the entire mechanism to be confined within the circumference of counter ring 2.

Figure 5:
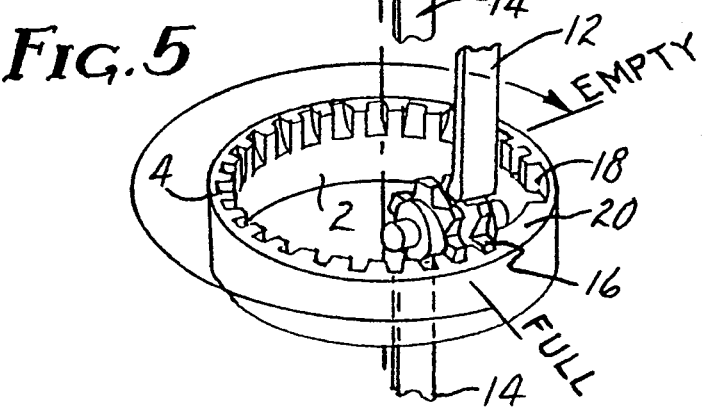

Referring to FIG. 5, movement of counter ring 2 can be stopped automatically at a position corresponding to an 'empty' vial by incorporating spacer gap 18 in teeth 4 of counter ring 2. Further rotation of counter ring 2 past the empty position can be positively prevented by the inclusion of spacer block 20.

Referring to FIG. 6, a breath actuated aerosol dispenser of the type disclosed in European Patent No. 147028 and commercially available under the trade name AUTOHALER ™ aerosol inhalation device from Minnesota Mining and Manufacturing Company comprises housing 24 incorporating a patient port, hereinafter referred to as mouthpiece 26 enclosed by removable cover 28 and containing aerosol vial 30. In alternative embodiments (not shown), dispenser 22 can have an integral nasal adapter, or be supplied with both mouthpiece and adaptor in an interchangeable format. Aerosol vial 30 can be of any suitable size and has a metering valve (not shown) possessing hollow valve stem 32. Valve stem 32 is located within socket 34 in support block 36 which has a passage 38 in communication with mouthpiece 26. Discharge of the metering valve is effected by relative movement between aerosol vial 30 and valve stem 32.

The breath actuation mechanism comprises vane 40 pivotally mounted within mouthpiece 26, and rocker element 42 which supports catch 44 pivotally mounted on rocker element 42 at 46. When the breath actuation mechanism is in its blocking, inoperative position, as shown in FIG. 6, and a cocking force is applied in the direction of arrow 'A', the movement of aerosol vial 30 is prevented. Such movement is blocked by rocker element 42 which is itself blocked from pivotal movement by catch 44 having curved surface 48 engaging curved surface 50 of vane 40. Thus, it is not possible to dispense the contents of aerosol vial 30 before the patient has inhaled through mouthpiece 26.

When a patient inhales through mouthpiece 26, inhalation causes pivotal movement of vane 40. The fully displaced position of vane 40 is depicted in dotted relief and denoted by 52. Curved surface 50 of vane 40 and curved surface 48 of catch 44 effectively act as cooperating roller surfaces such that pivotal movement of vane 40 causes curved surface 50 of vane 40 to rotate in one direction resulting in curved surface 48 of catch 44 rotating in the opposite direction. Catch 44 is displaced from a blocking to an unblocking position allowing for pivotal movement of rocker element 42 which, in turn, allows movement of aerosol vial 30 relative to valve stem 32 under the influence of the cocking pressure, thereby causing the valve to fire. Rocker element 44 is biased, e.g., by a spring, to the home (blocking) position when patient inspiration is halted.

Dispenser 22 is fitted with an indicator assembly to provide an indication of the quantity of doses dispensed from and/or the quantity of doses remaining in vial 30. The indicator assembly comprises: counter ring 2 having a plurality of circumferential teeth 4 and mounted for rotation about support block 36 with no appreciable axial movement thereof, the axis of rotation being substantially the same as the longitudinal axis of aerosol vial 30; and a reduction gear comprising shaft 6 bearing worm 8 and having at one end thereof integral ratchet wheel 10, shaft 6 being mounted for rotation about an axis transverse to the longitudinal axis of aerosol vial 30. Rocker element 42 is provided with actuating finger 12 which selectively engages ratchet wheel 10 upon displacement of element 42 during each actuation of dispenser 22 as described above, thereby causing the reduction gear to rotate a predetermined amount. Worm 8 engages teeth 4 of counter ring 2 and converts rotation of the reduction gear into incremental movement of counter ring 2. Support block 36 is provided with a flexible 'non-return' finger 14 which engages ratchet wheel 10 of the reduction gear to prevent unwanted (clockwise) rotation of the same during the return stroke of actuating finger 12, or in the course of handling and transport.

Suitable indicator markings are provided on the side of counter ring 2 which can be viewed through transparent window 54 in housing 24 to provide the patient with an indication of the contents remaining. For example, the counter ring can be numerically marked with each actuation, either descending to represent the quantity of doses remaining, or ascending to represent the quantity of doses used, with the present dosage being viewed through the housing window. A vial "EMPTY" and optionally a vial "FULL" sign can also be provided. In the simplest embodiment, the empty status of the vial can be represented by a change in colour. For example, the counter ring can be moulded in a green material with a vertical red stripe printed upon it. Initially, the red stripe would be set just to one side of the counter window and as the dispenser is used, the stripe is rotated away from the window until it eventually approaches it from the other side. As the last few doses are used, the red stripe will begin to appear in the counter window to indicate to the patient that the dispenser is nearly empty. Alternatively, the counter ring can be viewed through the mouthpiece.

Referring to FIG. 7, support block 36 of the aerosol dispenser shown in FIG. 6 is provided with a modified reduction gear, in which the ratchet wheel and worm are combined to produce 'toothed' worm 16.

Referring to FIG. 8, aerosol dispenser 55 comprises housing 24 defining inner chamber 56 and having integral mouthpiece 26. The dispenser additionally comprises aerosol vial 30 displaceably mounted within chamber 56 so that valve stem 32 abuts support block 36. The support block communicates with mouthpiece 26 through connecting passage 58 and valve stem 32 through socket 34. In use, mouthpiece 26 is inserted by the patient into his/her mouth and aerosol vial 30 fully depressed by the application of pressure to the base of aerosol vial 30 while the patient simultaneously inhales. Depression of aerosol vial 30 relative to valve stem 32 causes a metered dose to exit through support block 36 to mouthpiece 26. Patient inspiratory effort delivers the aerosolised medicament into the patient's pulmonary system. Valve stem 32 is biased, e.g., by a spring (not shown), to return aerosol vial 30 to the closed position when the displacing pressure is removed.

Dispenser 55 is provided with an indicator assembly comprising adaptor 60 which locates around support block 36 to support counter ring 2, the ring being mounted for rotation about support block 36; and a worm (reduction) gear comprising shaft 6 bearing worm 8 and ratchet wheel 10. Adaptor 60 is also provided with actuating finger 12. Valve stem 32 passes through channel 62 in finger 12, which is selectively engaged by depressed aerosol vial 30 via lug 64. Actuating finger 12, in turn, engages ratchet wheel 10 thereby rotating the reduction gear. As described above for the dispenser shown in FIG. 6, worm 8 of the reduction gear meshes with teeth 4 of counter ring 2 to convert rotation of the reduction gear into incremental movement of the counter ring. Housing 24 is provided with 'non-return' finger 14 to prevent unwanted (counterclockwise) rotation of ratchet wheel 10. In this embodiment, counter ring 2 is viewed by the patient through mouthpiece 26.

Referring to FIGS. 9 to 11, an alternative arrangement of indicator assembly is shown for use with the aerosol dispenser of FIG. 8. The indicator assembly comprises adaptor 60, counter ring 2 mounted for rotation about the periphery of adaptor 60 and having a plurality of circumferential teeth 4, a reduction gear comprising shaft 6 bearing worm 8 and having at either end thereof ratchet wheel 10 and 66 and a movement detecting member comprising base portion 68, ring-shaped portion 70 and two resiliently flexible members 72 and 74.

Adaptor 60 comprises circular base 76 having central boss 78 which is complementary in shape to support block 36 of the aerosol dispenser. During assembly, adaptor 60 is located about support block 36 as shown in FIG. 10 and serves to support the remainder of the indicator assembly. Central boss 78 of adaptor 60 is provided with channel 62 which allows the valve stem of the aerosol vial (not shown) to be inserted into socket 34 of support block 36.

Counter ring 2 is formed with peripheral groove 80 which supports ring 2 on base 76 of adaptor 60 to permit rotation thereof. Flange 82 and retaining clips 84 secure counter ring 2 in position to prevent unwanted lateral and axial movement of the ring.

Base portion 68 of the movement detecting member is pivotally mounted at 86 to permit displacement of the member in the direction indicated by the solid arrow labelled E (see FIG. 10). When the dispenser is not in use, displacement of the movement detecting member as indicated is prevented by resiliently flexible members 72 and 74 which abut support columns 88 and 90.

Ring shaped portion 70 of the movement detecting member extends around central boss 78 and support block 36 and is provided with actuating finger 12 which is selectively engageable with ratchet wheel 10 of the reduction gear and projecting lugs 92 and 94 which are, in turn, selectively engageable by the aerosol vial. To use the dispenser the patient inserts the mouthpiece (not shown) into his or her oral or nasal cavity and depresses the aerosol vial relative to the valve stem by the application of pressure to the base of the vial, thereby causing a metered dose to exit through support block 36 to the mouthpiece. Subsequent patient inspiration delivers the aerosolised medicament into the lungs. In this manner, depression of the aerosol vial by the patient causes the vial to engage lugs 92 and 94 of ring-shaped portion 70 of the movement detecting member, thereby displacing the member. This enables actuating finger 12 to engage ratchet wheel 10 of the reduction gear, thereby rotating the reduction gear. Worm 8 of the reduction gear meshes with teeth 4 of counter ring 2 to convert rotation of the reduction gear into incremental movement of counter ring 2.

Displacement of the movement detecting member produces an antagonistic tension in resiliently flexible members 72 and 74 which on the return of the aerosol vial to its home position (the displacing pressure having been removed) causes the movement detecting member to return to its home position.

Adaptor 60 is provided with a flexible non-return finger 14 which engages the other ratchet wheel 66 of the reduction gear to prevent unwanted rotation of the same during the return stroke of actuating finger 12.

We claim:

1. An aerosol dispenser comprising a housing having a patient port, the housing being adapted to accommodate an aerosol vial equipped with a metered-dose dispensing valve that comprises a valve stem movable between closed and discharge positions, the dispenser further comprising a support block having a socket adapted to receive a valve stem and an orifice having open communication with the socket and the patient port, the support block being reciprocally movable relative to an aerosol vial accommodated within the housing, the dispenser having an indicator assembly comprising a rotatable indicator, the indicator comprising a circumferential rack and being mounted for rotation about an axis parallel to said reciprocal movement of the support block relative to an aerosol vial accommodated within the housing; a worm-gear engaging said circumferential rack, and a movement detecting member movable in response to said reciprocal movement, wherein movement of the movement detecting member in response to said reciprocal movement causes rotation of said worm gear and indicator.

2. An aerosol dispenser according to claim 1 in which the indicator comprises an annular rack.

3. An aerosol dispenser according to claim 2 in which the indicator comprises an annular rack mounted for rotation about the support block.

4. An aerosol dispenser according to claim 2 in which the rack comprises teeth, a spacer gap, and a spacer block to prevent more than one full rotation of the rack.

5. An aerosol dispenser according to claim 2 in which the rack comprises teeth and the worm-gear comprises a shaft bearing a worm mounted for rotation about an axis transverse to said reciprocal movement, the shaft further comprising an integral ratchet wheel which is selectively engageable by said movement detecting member to rotate the worm-gear, the worm meshing with the teeth of the rack to drive the rack upon said rotation.

6. An aerosol dispenser according to claim 5 in which the worm and ratchet wheel are integral.

7. An aerosol dispenser according to claim 1 in which the movement detecting member comprises a projecting finger fixed relative to one of an aerosol vial accommodated within the housing and said support block and selectively engageable with said worm-gear.

8. An aerosol dispenser according to claim 7 in which the projecting finger is fixed relative to the aerosol vial and said vial is movable relative to the support block.

9. An aerosol dispenser according to claim 7 in which the projecting finger is fixed relative to the support block and said vial is movable relative to the support block to selectively engage the projecting finger.

10. An aerosol dispenser according to claim 1 in which the movement detecting member comprises an aerosol vial accommodated within the housing.

11. An aerosol dispenser according to claim 1 in which the housing is provided with a viewing port through which the indicator is visible.

12. An aerosol dispenser according to claim 1 in which the indicator is visible through the patient port.

13. An aerosol dispenser according to claim 1 in which the indicator assembly further comprises means to prevent unwanted movement of the indicator means.

14. An aerosol dispenser according to claim 1 further comprising means to prevent actuation of an aerosol vial accommodated within the chamber prior to inhalation through the dispenser.

15. An aerosol dispenser according to claim 1 in combination with an aerosol vial.

16. An aerosol dispenser according to claim 1 in combination with an aerosol vial, said aerosol vial containing a self-propelled pharmaceutical formulation comprising a medicament.

* * * * *